United States Patent
Chong

(10) Patent No.: US 7,262,224 B2
(45) Date of Patent: Aug. 28, 2007

(54) COSMETIC REJUVENATING AND HEALING PRODUCT, METHOD OF ITS MANUFACTURE AND USES THEREOF

(75) Inventor: Myong Hun Chong, Arlington, TX (US)

(73) Assignee: Hanna Isul Skin Therapy, Inc., Fort Worth, TX (US)

( * ) Notice: Subject to any disclaimer, the term of this patent is extended or adjusted under 35 U.S.C. 154(b) by 515 days.

(21) Appl. No.: 10/359,963

(22) Filed: Feb. 6, 2003

(65) Prior Publication Data

US 2003/0223953 A1 Dec. 4, 2003

Related U.S. Application Data

(63) Continuation-in-part of application No. 09/723,884, filed on Nov. 28, 2000, now abandoned.

(60) Provisional application No. 60/168,257, filed on Nov. 30, 1999.

(51) Int. Cl.
*A61K 31/07* (2006.01)
*A61K 31/375* (2006.01)
*A61K 31/593* (2006.01)
*A61K 31/355* (2006.01)

(52) U.S. Cl. .................... 514/904; 514/52; 514/167; 514/168; 514/458; 514/474; 514/725; 424/401

(58) Field of Classification Search ............... 424/401, 424/725, 736, 744; 514/725, 944
See application file for complete search history.

(56) References Cited

U.S. PATENT DOCUMENTS

| 4,369,180 | A | * | 1/1983 | Mihalovits ............. 514/21 |
| 5,653,970 | A | * | 8/1997 | Vermeer ............. 424/70.24 |
| 5,993,792 | A | * | 11/1999 | Rath et al. ............. 424/70.28 |
| 5,997,889 | A | * | 12/1999 | Durr et al. ............. 424/401 |
| 6,495,122 | B2 | | 12/2002 | Frankhauser et al. ......... 424/59 |
| 6,630,163 | B1 | | 10/2003 | Murad ............. 424/464 |

FOREIGN PATENT DOCUMENTS

WO WO84/02845 * 8/1984

OTHER PUBLICATIONS

Flick, E., Cosmetic and Toiletry Formulations, 1995, vol. 4 (2nd Ed.), p. 306.*

* cited by examiner

*Primary Examiner*—Sreeni Padmanabhan
*Assistant Examiner*—Gina C. Yu
(74) *Attorney, Agent, or Firm*—Charles D. Gunter, Jr.

(57) ABSTRACT

A cosmetic composition is shown for rejuvenating the appearance of skin with reduced or minimal potential for skin irritation, in the form of a lotion or cream which includes as a major component aloe vera as well as vitamins A, B, C, D and E.

1 Claim, No Drawings

COSMETIC REJUVENATING AND HEALING PRODUCT, METHOD OF ITS MANUFACTURE AND USES THEREOF

1. CROSS REFERENCE TO RELATED APPLICATIONS

This application is a continuation-in-part of earlier filed Ser. No. 09/723,884, filed Nov. 28, 2000 now abandoned, which application claims priority based upon provisional application No. 60/168,257, filed Nov. 30, 1999, by the same inventor and entitled "Cosmetic Rejuvenating and Healing Product, Method For Its Manufacture and Uses Thereof."

BACKGROUND OF THE INVENTION

2. Field of the Invention

The present invention relates to a cosmetic composition for rejuvenating the appearance of skin with reduced or minimal potential for skin irritation, preferably in the form of a lotion or creme, which includes as a major component aloe vera as well as Vitamins A, B, C, D and E.

3. Description of the Prior Art

Conventional treatment of, or attempted prevention of, normal tissue damage caused by, for example, UV radiation of the sun, over-exfoliated, peeled and lasered skin tissue, and the like, is currently confined to the application of bland moisturizing creams designed only to minimize infection to the damaged site or to prevent itching and subsequent scratching by the affected individual. Such treatment can at best only offer symptomatic relief and a barrier to assist prevention of secondary infection at the affected site.

Additionally, conventional creams or ointments are designed to deliver an active component only to the epidermal surface of the skin or, at best, to provide limited delivery through the surface skin layers. Most cosmetic formulations currently available utilize an intimate dispersion or solution of the active components or components in a suitable oily medium or a water/oil or oil/water emulsion. Thus the formulation is presented to the epidermal surface in a form likely to penetrate only into the outer layer of the epidermis.

A need exits, therefore, for a cosmetic formulation which will treat all skin types deep beneath the surface layer of the epidermis to restore, balance and hydrate the skin, returning the skin to its normal, healthy level.

A need also exists for such a cosmetic formulation which exhibits a similar beneficial effect when applied to burns, stings, rashes, infections, acne and other skin irritations.

A need also exists for such a cosmetic formulation which relieves itching and other discomforts suffered after laser or face lift surgery and glycolic or chemical peels which acts swiftly to aid the healing process immediately upon contact.

A need exists for such a cosmetic formulation which contains non-oily, natural ingredients yet exhibits an extended shelf life without prematurely degrading.

A need also exists for such a formulation which contains a sun supplement to help protect the skin from damage from the harmful effects of the sun.

SUMMARY OF THE INVENTION

The present invention is a cosmetic composition for rejuvenating the appearance of skin with reduced or minimal potential for skin irritation, preferably in the form of a lotion or cream, which includes as a major component aloe vera as well as Vitamins A, B, C, D and E. Preferably, the cosmetic composition contains greater than about 50% aloe vera and as well as each of the vitamins A, B, C, D and E as an essential component. The major components of the composition are non-oily, natural ingredients and yet the formulation of the invention has an extended shelf life. The non-oily nature of the formulation allows the active ingredients to penetrate the human epidermis to a greater relative depth than prior oil-based formulations.

Additional objects, features and advantages will be apparent in the written description which follows.

DETAILED DESCRIPTION OF THE INVENTION

The cosmetic formulations of the invention aid in relieving skin irritation, acne, swelling, bruising, infection, burns, stings and rashes of the epidermis. The cosmetic formulations are also beneficial in treating the deleterious effects of glycolic or chemical peels, and relieve itching after laser surgery or face lift surgery immediately upon contact. While other products cleanse and moisturize at the surface level, the formulations of the present invention restore, balance and hydrate the human epidermis at a deeper level, returning it to its normal healthy state.

The cosmetic formulations of the invention utilize pure botanical essences and vitamins to provide gentle, fragrant and soothing compositions which aid the skin's ability to heal itself. The formulations of the invention nurture and nourish the skin so that within a short period of time the skin appears younger, healthier, more firm and glowing. For the first time, Applicant has combined each of the vitamins A, B, C, D and E as an essential component within a natural ingredient based recovery ointment which has an extended shelf life.

The formulations of the invention contain a natural base ingredient which is combined with other ingredients to achieve a synergistic result. The base ingredient is aloe vera extract.

Aloe vera is a well known extract from the aloe plant and occurs naturally in nature. The aloe leaf consists of three primary sections: the rind (photosynthesis) with sap contained in the pericyclic transport tubules (xylem and phloem), the mucilage (container) layer and the parenchyma or gel fillet (storage) layer. It is believed that the beneficial properties of the plant extract are the result of the synergistic actions of at least 75 known ingredients, including polysaccharides, steroids, organic acids, enzymes, antibiotic agents, amino acids and minerals. Glucomannan, one special complex polysaccharide composed largely of the sugar mannose, interacts with special cell-surface receptors on those cells which repair damaged tissues, called fibroblasts, stimulating them, activating their faster growth and replication. Plant hormones in aloe, called gibberellins, also accelerate healing by cell replication. Various other beneficial effects of the aloe vera plant extract are reported in the literature. The aloe vera component of Applicant's formulation is present in the range from about 50-75% by volume, preferably in an amount greater than about 50% by volume, and most preferably about 60% by volume, based upon the total volume of the cosmetic formulation.

Applicant's cosmetic formulations present the positive healing properties of the aloe extract in combination with a synergistic active ingredient formulation which allows the active ingredients to penetrate more deeply into the epidermis to provide a deeper, longer lasting healing effect. The additional components of the formulation will be discussed in turn below.

Deionized water is purified water having almost all solids removed by an ion-exchange process and is widely used in the laboratory environment. It is present in the range from about 5 to 25%, most preferably about 15.5% by volume, based upon the total volume of the cosmetic formulation.

Cetearyl alcohol, also known as cetostearyl alcohol, and polysorbate 60 (polyoxyethylene sorbitan monostearate) are emollient and emulsion stabilizers used in many cosmetic preparations. This component of the formulation of the invention is preferably present in the range from about 0.1 to 5% by volume, most preferably about 1% by volume.

Isopropyl palmitate is a mixture of solid organic acids obtained from fats consisting chiefly of palmitic acid with varying amounts of stearic acid. It is used in various products as an emollient and texturizer. This component is present in the range from about 2 to 5%, most preferably about 3%.

Glycerine is a viscous, crystalline liquid formed when fat molecules split, forming free fatty acids and glycerine. It is commercially available from a number of sources and serves as a humectant. Glycerine is present in the range from about 1 to 5% by volume, most preferably about 3% by volume.

Cetyl alcohol is an emollient and emulsion stabilizer used in various cosmetic compositions and is present in the range from about 2 to 7% by volume, most preferably about 5% by volume.

Shea butter is a slightly ivory granulated butter consisting of mostly triglycerides, including a fair amount of linoleic acid, and unsaponifiables. It is present in the formulations of the invention in the range from about 1 to 5% by volume, most preferably about 2% by volume, based upon the total volume of the formulation.

The glyceryl stearate/PEG 100 Stearate are commercial emulsifiers present in the range from about 1 to 5%, most preferably about 3% by volume.

Cyclomethicone is a widely used silicone agent found in hair and skin care products and is present in the formulations of the invention in the range from about 0.5 to 5% by volume, preferably about 2% by volume.

The phenoxyethanol, methylparaben, ethylparaben, butylparaben, propylparaben and isobutylparaben components of the formulations of the invention are commercially available preservatives present in the range from about 0.5 to 3%, most preferably about 0.7% by volume.

The jojoba oil component of the formulations of the invention is an oil extracted from the bean-like seeds of the desert shrub, *Simondsia Chinensis*. It can be pressed into a golden, naturally liquid wax. As a lubricant, it has been used in the past as a substitute for carnauba wax and beeswax. It is present in the formulations of the invention in the range from about 0.5 to 3%, most preferably about 1% by volume.

Avocado oil is extracted from the fruit of the tree, *Persea americana*. It is a vegetal oil used in moisturizers and facial creams. It is clear, light and non-tacky with quick penetration characteristics. It is present in the range from about 0.1 to 3% by volume, preferably about 0.5% by volume.

Lanolin oil is a yellowish-white fatty substance obtained from the wool of sheep. This component is present in the range from about 0.1 to 3% by volume, preferably about 0.5% by volume.

Hydrogenated Castor Oil, $C_3H_5(C_{18}H_{35}O_3)_3$, is widely used for manufacturing cosmetics, shoeshines and other products as well as for making 12-hydroxy stearic acid. It is present in the range from about 01. to 3%, most preferably about 0.5%.

Demethicone is another commercially available silicone agent used as an ointment base. It is present in the range from about 0.1 to 3% by volume, preferably about 1% by volume.

Tocopheryl acetate is a source of Vitamin E. It has known antioxidant properties and is present in the range from about 0.1 to 2% by volume, preferably about 0.2% by volume.

Orange oil is used as a flavor or scent additive and contains enzymes which purify the skin in the formulations of the invention and is present in the range from about 0.1 to 2% by volume, preferably about 0.5% by volume.

Panthenol, also known as dexpanthenol is a Vitamin B complex factor used in hair products and in emollients. It is present in the range from about 0.1 to 2% by volume, preferably about 0.2% by volume.

Retinyl palmitate is the ester of Vitamin A and palmitic acid. It is present in the range from about 0.1 to 1% by volume, preferably about 0.2% by volume.

Cholecalciferol or ergocalciferol is a white, colorless crystal found in plants and years having Vitamin D activity. It is present in the range from about 0.05 to 0.5% by volume, preferably about 0.1% by volume.

Ascorbyl palmitate is an anti-oxidant and source of Vitamin C and is present in the formulations of the invention in the range from about 0.05 to 2% by volume, most preferably about 0.1% by volume.

In a particularly preferred form, the cosmetic rejuvenating formulation of the invention comprises:

| RECOVERY OINTMENT | | |
|---|---|---|
| INGREDIENTS | FUNCTION | PERCENTAGE |
| 1. ALOE VERA GEL | MOISTURIZER, HEALING | 60% |
| 2. DEIONIZED WATER | SOLVENT | 15.5% |
| 3. CETYL ALCOHOL | EMULSIFIER | 5% |
| 4. GLYCERIN | HUMECTANT | 3% |
| 5. ISOPROPYL PALMITATE | EMOLLIENT | 3% |
| 6. GLYCERYL STEARATE/PEG 100 STEARATE | EMULSIFIER | 3% |
| 7. SHEA BUTTER | EMOLLIENT | 2% |
| 8. CYCLOMETHICONE | EMOLLIENT | 2% |
| 9. JOJOBA OIL | EMOLLIENT | 1% |
| 10. CETEARYL ALCOHOL AND POLYSORBATE 60 | EMULSIFIER | 1% |
| 11. DEMETHICONE | EMOLLIENT | 1% |

-continued

RECOVERY OINTMENT

| INGREDIENTS | FUNCTION | PERCENTAGE |
|---|---|---|
| 12. PHENOXYETHANOL, METHYLPARABEN, ETHYLPARABEN, BUTYLPARABEN, PROPYLPARABEN AND ISOBUTYLPARABEN | PRESERVATIVE | 0.7% |
| 13. AVOCODO OIL | EMOLLIENT | 0.5% |
| 14. LANOLIN OIL | EMOLLIENT | 0.5% |
| 15. PEG-40 HYDROGENATED CASTOR OIL | SOLUBILIZER | 0.5% |
| 16. ORANGE OIL | FRAGRANCE | 0.5% |
| 17. DL PANTHENOL | HUMECTANT, VITAMIN B5 | 0.2% |
| 18. TOCOPHERYL ACETATE | ANTIOXIDANT, VITAMIN E | 0.2% |
| 19. RETINYL PALMITATE | SKIN PROTECTANT, VITAMIN A | 0.2% |
| 20. CHOLECALCIFEROL V-D | ABSORPTION, VITAMIN D | 0.1% |
| 21. ASCORBYL PALMITATE | ANTIOXIDANT, VITAMIN C | 0.1% |

An invention has been provided with several advantages. The formulations of the invention contain non-oily, natural ingredients that penetrate the epidermis to provide improved healing properties for skin irritations, acne, bruising and swelling as well as the inflammation caused from trauma to the skin following surgical procedures. The formulations assist in burn healing and in the treatment of stings, rashes, eczema, psoriasis and heat rash. Despite the use of natural active ingredients, the formulations of the invention have an extended shelf life of 3 years or more. The unique combination of Vitamins A, B, C, D and E produces a synergistic effect in achieving the desired results mentioned above.

While the invention has been shown in only one of its forms, it is not thus limited but is susceptible to various changes and modifications without departing from the spirit thereof.

I claim:

1. A method of providing transdermal delivery of active skin care ingredients to living cells in a human's skin dermis for rejuvenating the appearance of the human epidermis with reduced or minimal potential for skin irritation, in the form of a cream which includes as a major component aloe vera as well as vitamins A,B,C,D and E, the method consisting essentially of the steps of:

formulating a cosmetic cream comprising, as active ingredients:
a non-oily base comprising greater than about 50% by volume, based upon the total volume of the formulation, of aloe vera extract;
from about 0.1 to 1.0% by volume of tocopheryl acetate as a source of Vitamin E;
from about 0.1 to 0.5% by volume of retinyl palmitate as a source of Vitamin A;
from about 0.05 to 0.5% by volume of ascorbyl palmitate as a source of Vitamin C;
from about 0.1. to 2.0% panthenol as a source of Vitamin B;
from about 0.05 to 0.5% cholecalciferol as a source of Vitamin D;
the balance being emulsifier, emollients and preservatives;
applying the cosmetic cream to an area of exposed skin of the human, the formulation being effective to achieve transdermal delivery of the active ingredients by penetrating the human epidermis to a greater relative depth than oil-based topical cosmetic formulations.

* * * * *